United States Patent
Rajule et al.

(10) Patent No.: US 10,696,610 B2
(45) Date of Patent: Jun. 30, 2020

(54) SCALABLE SYNTHESIS OF HYDROGENATED ALPHA STYRENE DIMER

(71) Applicant: VALVOLINE LICENSING AND INTELLECTUAL PROPERTY LLC, Lexington, KY (US)

(72) Inventors: Rajkumar Rajule, Dist. Thane (IN); Jesse Dambacher, Lexington, KY (US)

(73) Assignee: VALVOLINE LICENSING AND INTELLECTUAL PROPERTY LLC, Lexington, KY (US)

(*) Notice: Subject to any disclaimer, the term of this patent is extended or adjusted under 35 U.S.C. 154(b) by 0 days.

(21) Appl. No.: 16/214,867

(22) Filed: Dec. 10, 2018

(65) Prior Publication Data

US 2019/0177249 A1    Jun. 13, 2019

Related U.S. Application Data

(60) Provisional application No. 62/597,149, filed on Dec. 11, 2017.

(51) Int. Cl.
| | | |
|---|---|---|
| C07C 5/10 | (2006.01) | |
| C07C 7/12 | (2006.01) | |
| G01N 30/92 | (2006.01) | |
| B01D 15/10 | (2006.01) | |

(52) U.S. Cl.
CPC ............ *C07C 5/10* (2013.01); *C07C 7/12* (2013.01); *G01N 30/92* (2013.01); *B01D 15/10* (2013.01); *C07C 2523/46* (2013.01); *C07C 2601/14* (2017.05)

(58) Field of Classification Search
CPC .. C07C 13/28; C07C 5/10; C07C 7/12; C07C 2523/46; C07C 2601/14; B01D 15/10; G01N 30/92
See application file for complete search history.

(56) References Cited

U.S. PATENT DOCUMENTS

| | | |
|---|---|---|
| 2,530,774 A | 11/1950 | Kehe et al. |
| 3,646,235 A | 2/1972 | Little et al. |
| 3,677,970 A | 7/1972 | Mertzweiller et al. |
| 4,199,481 A | 4/1980 | Hall et al. |
| 4,410,755 A * | 10/1983 | Fisher ............... C07C 7/163 568/749 |
| 5,973,206 A | 10/1999 | Laitinen |
| 6,488,898 B1 | 12/2002 | Lee et al. |
| 2013/0150626 A1 | 6/2013 | Mertens et al. |
| 2014/0350038 A1 * | 11/2014 | Reddy ............... C07D 239/48 514/275 |

FOREIGN PATENT DOCUMENTS

| | | |
|---|---|---|
| CN | 102964199 B | 12/2014 |
| JP | 60001354 B2 | 1/1985 |
| JP | 60096690 A | 5/1985 |
| JP | 60043392 B2 | 9/1985 |
| JP | 61051095 A | 3/1986 |
| JP | 63039986 A | 2/1988 |
| JP | 63213597 A | 9/1988 |
| JP | 1046494 B2 | 10/1989 |
| JP | 2018717 B2 | 4/1990 |
| JP | 2018719 B2 | 4/1990 |
| JP | 3080190 B2 | 12/1991 |
| JP | 4000518 B2 | 1/1992 |
| JP | 4001795 B2 | 1/1992 |
| JP | 4007734 B2 | 2/1992 |
| JP | 4034978 B2 | 6/1992 |
| JP | 4068293 B2 | 11/1992 |
| JP | 4075895 B2 | 12/1992 |
| JP | 5031914 B2 | 5/1993 |
| JP | 5062918 B2 | 9/1993 |
| JP | 6008425 B2 | 2/1994 |
| JP | 6051874 B2 | 7/1994 |
| JP | 6062984 B2 | 8/1994 |
| JP | 6092593 A | 11/1994 |
| JP | 7010992 B2 | 2/1995 |
| JP | 7029946 B2 | 4/1995 |
| JP | 7029947 B2 | 4/1995 |
| JP | 7103387 B2 | 11/1995 |

(Continued)

OTHER PUBLICATIONS

B. Chaudhuri et al., Some Novel Aspects of the Dimerization of α-Methylstyrene with Acidic Ion-Exchange Resins, Clays and other Acidic Materials as Catalysts, Ind. Eng. Chem. Res., vol. 28, No. 12: 1989, pp. 1757-1763.

T. Tsubouchi, et al., Quantitative Correlation Between Molecular Structures of Traction Fluids and Their Traction Properties (Part 1): Influence of Alkylene Chain, Japanese Journal of Tribology, vol. 38, No. 3: 1993,pp. 403-410.

T. Tsubouchi, et al., Optimisation of Molecular Structure for Traction Fluids, Lubrication Scienc, ISSN 0954-0075: Aug. 2004, pp. 393-403.

International Search Report and Written Opinion issued in PCT application PCT/US2018/064710, dated Feb. 21, 2019.

*Primary Examiner* — Sharon Pregler
(74) *Attorney, Agent, or Firm* — Benesch Friedlander Coplan & Aronoff LLP

(57) ABSTRACT

A procedure for hydrogenation of alpha dimethyl styrene dimer that is scalable, economical, and safe is provided. These processes routinely provide greater than a 98% yield and require no purification step. The methods of producing hydrogenated alpha dimethyl styrene dimer comprising adding to a reactor under nitrogen a catalyst comprising Ru/C or Rh/C and an alpha dimethyl styrene dimer to form a catalyst and alpha dimethyl styrene dimer reaction mixture. The reaction mixture is then heated under pressure until hydrogenation of the alpha dimethyl styrene dimer is complete. To recover the hydrogenated alpha dimethyl styrene dimer, the reaction mixture is filtered through a celite bed under nitrogen.

20 Claims, 3 Drawing Sheets

(56) References Cited

FOREIGN PATENT DOCUMENTS

| | | |
|---|---|---|
| JP | 02546796 B2 | 10/1996 |
| JP | 02561758 B2 | 12/1996 |
| JP | 02809448 B2 | 10/1998 |
| JP | 02888734 B2 | 5/1999 |
| JP | 2000087069 A | 3/2000 |
| JP | 2001261589 A | 9/2001 |
| JP | 2002114714 A | 4/2002 |
| JP | 03599231 B2 | 12/2004 |
| JP | 2005170903 A | 6/2005 |
| JP | 2007146017 A | 6/2007 |
| JP | 04044225 B2 | 2/2008 |
| JP | 04145999 B2 | 9/2008 |
| JP | 04166309 B2 | 10/2008 |
| JP | 04184767 B2 | 11/2008 |
| JP | 04354070 B2 | 10/2009 |
| JP | 04377687 B2 | 12/2009 |
| JP | 04422286 B2 | 2/2010 |
| JP | 04448709 B2 | 4/2010 |
| JP | 04456718 B2 | 4/2010 |
| JP | 04521275 B2 | 8/2010 |
| JP | 04560157 B2 | 10/2010 |
| JP | 04562906 B2 | 10/2010 |
| JP | 04675779 B2 | 4/2011 |
| JP | 04700288 B2 | 6/2011 |
| JP | 04792171 B2 | 10/2011 |
| JP | 04891469 B2 | 3/2012 |
| JP | 04938250 B2 | 5/2012 |
| JP | 04999320 B2 | 8/2012 |
| JP | 05431657 B2 | 3/2014 |
| JP | 2015172135 A | 10/2015 |
| JP | 05816497 B2 | 11/2015 |
| JP | 05872946 B2 | 3/2016 |
| JP | 2016030803 A | 3/2016 |
| JP | 06182480 B2 | 8/2017 |
| JP | 2017160407 A | 9/2017 |
| JP | 2019131637 A | 8/2019 |

* cited by examiner

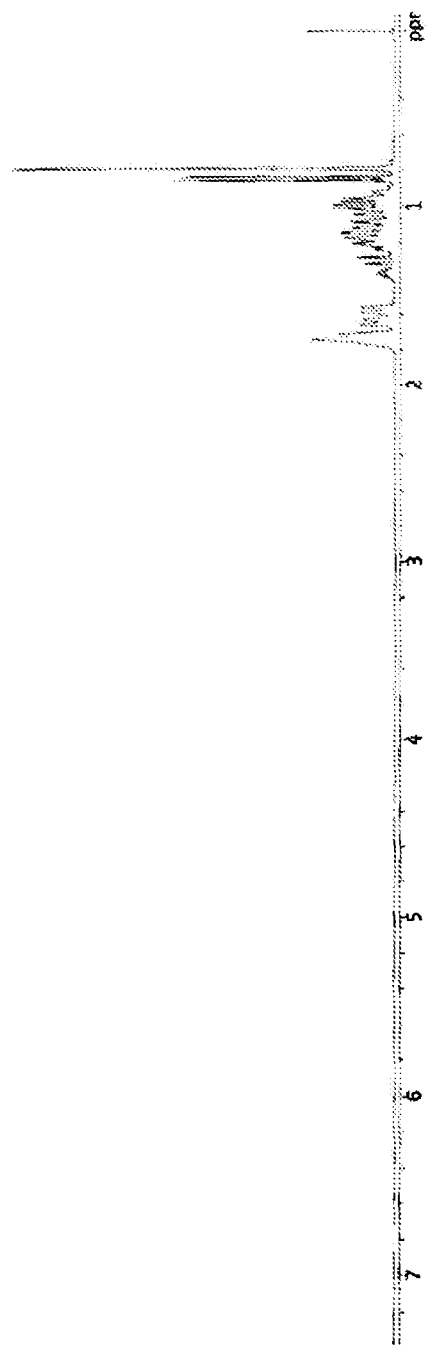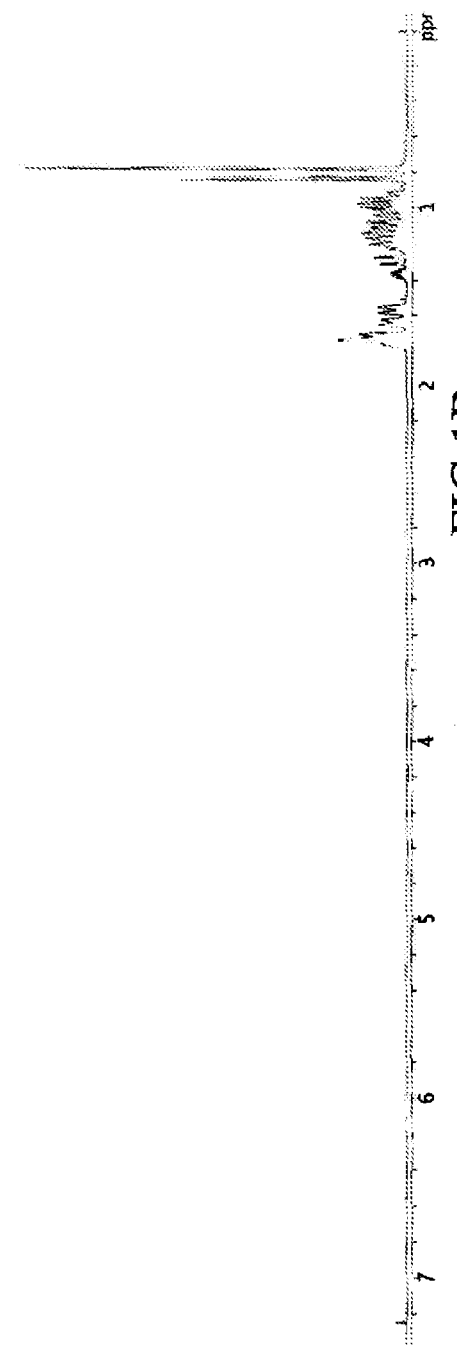

SCALABLE SYNTHESIS OF HYDROGENATED ALPHA STYRENE DIMER

RELATED APPLICATIONS

This application claims priority to U.S. Provisional Patent Application No. 62/597,149 filed Dec. 11, 2017.

FIELD OF INVENTION

The present disclosure generally relates to a method of economically making hydrogenated alpha dimethyl styrene.

BACKGROUND

In the year 1999, toroidal continuous variable transmission (T-CVT) cars were introduced in the market and the traction fluid used for the T-CVT required high level of performance in terms of high traction coefficient and low temperature fluidity of the molecule. Tsubouchi et al. (*Lubrication Science* 2004, 16(4), 393-403) reported parameters for designing molecular structure with high traction coefficient including high molecular stiffness, large size, short alkylene chain length, high melting point and low molecular polarity for getting good traction coefficient. The industry uses specially designed traction fluid such as hydrogenated alpha dimethyl styrene (HAD), which has excellent traction coefficient and low temperature viscosity-key performance parameters including: Melting point −30° C., boiling point 112° C. (0.7 mm of Hg). The traction coefficient of HAD is reported as 0.058 at 140° C., with slide to roll ratio is 5% (*Japanese Journal of Tribology* Vol 38, 3, 1993). The chemical structure of HAD (2,4-dicyclohexyl-2-methylpentane) is presented in Formula I:

Formula I

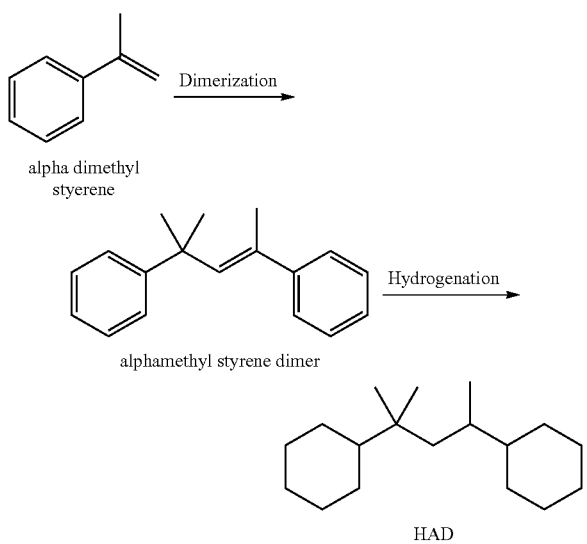

The synthesis of HAD involves two steps, alpha dimethyl styerene

Dimerization alphamethyl styrene dimer

Hydrogenation

HAD

The first step is dimerization. The dimerization reaction of alkene at a rate of nearly 100% in atom economical reaction has been reported in the prior art. Chaudhuri et al. (*Ind. Eng. Chem. Res.* 1989, 28, 1757-1763) reported comprehensive studies on the dimerization of alpha dimethyl styrene.

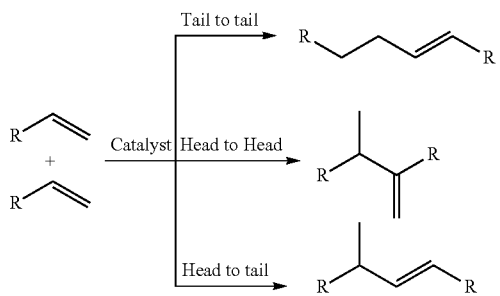

The second step for preparation of HAD is hydrogenation reaction. The molecular weight of the starting material, an alpha methyl styrene dimer is 236.36 and that of end product HAD is 250.47.

Most known chemical processes use Raney Nickel as catalyst, and reaction is carried out at very high temperature and pressure (Toshiyuki et al. EP0224259). Nickel is economical to use, with poor recyclability and have safety issues while handling at larger scale.

Therefore there is a need in the field to have a safe, green and economical process on bulk scale, with less loading of the catalyst and better yields.

SUMMARY

The present disclosure provides a scalable method for hydrogenation of alpha dimethyl styrene (AMS) dimers. The methods of the present disclosure produce yields of at least 90% from starting material and more preferably 98% yield from starting material AMS dimer in the absence of solvent. The methods disclosed effectuate hydrogenation of alpha dimethyl styrene dimers at lower temperatures and pressures than required for other catalytic methods and further at lowest loading of the catalyst, provide for recovery of the catalyst after the reaction is complete.

The method of producing hydrogenated alpha dimethyl styrene dimer includes adding to a Haste alloy reactor, with turbine impeller, under nitrogen, a catalyst including Ru/C or Rh/C and an alpha dimethyl styrene dimer to form a catalyst and alpha dimethyl styrene dimer reaction mixture. The reaction mixture is then heated under pressure until hydrogenation of the alpha dimethyl styrene dimer is complete. To recover the hydrogenated alpha dimethyl styrene dimer, the reaction mixture is filtered through a celite bed under nitrogen.

The time, pressure, temperature, amounts of catalyst and starting material may all be varied. The catalyst of the reaction may be recovered after reaction completion and can be used in the next batch with additional topping of fresh catalyst.

BRIEF DESCRIPTION OF THE DRAWINGS

In the accompanying figures, chemical formulas, chemical structures, and experimental data are given that, together with the detailed description provided below, describe example embodiments of the claimed invention.

FIG. 1(A)-(B) shows the NMR spectra for (A) commercially available standard hydrogenated alpha dimethyl styrene dimer and (B) a hydrogenated alpha dimethyl styrene dimer prepared according to the methods of the present disclosure, Example 1, sample number 2.

DETAILED DESCRIPTION

Figure 2A:
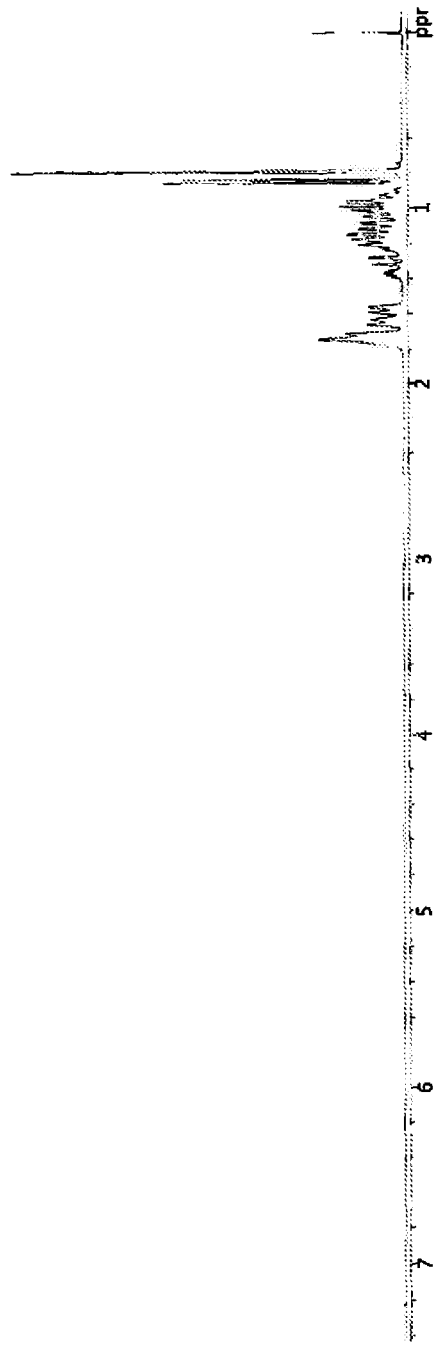
FIG. 2(A)-(B) shows the NMR spectra for (A) commercially available standard hydrogenated alpha dimethyl styrene dimer and (B) a hydrogenated alpha dimethyl styrene dimer prepared according to the methods of the present disclosure, Example 1, sample number 3.

A procedure for hydrogenation of alpha dimethyl styrene dimer that is scalable, economical, and safe will be described in detail. These procedures result in routinely greater than a 98% yield and require no purification step.

The methods of producing hydrogenated alpha dimethyl styrene dimer include adding to a Haste alloy reactor, with turbine impeller, under nitrogen a catalyst comprising Ru/C or Rh/C and an alpha dimethyl styrene dimer to form a catalyst and alpha dimethyl styrene dimer reaction mixture. The reaction mixture comprises the Ru/C or Rh/C catalyst and alpha dimethyl styrene dimer. Alternatively, the reaction mixture may consist essentially of Ru/C or Rh/C catalyst and alpha dimethyl styrene dimer or consist of Ru/C or Rh/C catalyst and alpha dimethyl styrene dimer. The reaction mixture is then heated under pressure until hydrogenation of the alpha dimethyl styrene dimer is complete. To recover the hydrogenated alpha dimethyl styrene dimer, the reaction mixture is filtered through a celite bed under nitrogen. The filtration step functions to remove the catalyst.

It is noted that this method of production is solventless. Therefore a step of distillation or other purification process step, which may have a significant operation cost when the reaction occurs on a larger scale, is unnecessary.

The resulting filtered hydrogenated alpha dimethyl styrene dimer product may be concentrated under a vacuum, though such a step is not required.

The hydrogenation reaction may be monitored for completion by performing thin layer chromatography on a sample of the reaction mixture. The reaction is complete when hydrogen consumption ceases. Likewise, a sample of the reaction mixture may be analyzed by the absence of an aromatic peak in a nuclear magnetic resonance (NMR) spectra. Gas chromatograph mass spectrometry (GCMS) or any other technique may also be used to evaluate the completeness of the hydrogenation reaction.

Several catalysts were screened for the scalable HAD synthetic methods, including Ru/C, Rh/C, complexes of Ru and Rh, Raney Nickel, and Pd(OH)$_2$/C. Raney Nickel and Pd(OH)$_2$/C failed to produce HAD and the lower temperature and pressure criteria of the preferred methods. The catalyst used in the present reaction may consist essentially of or consist of Ru/C or Rh/C. While the Ru or Rh are preferably on a carrier material, they may be used in other forms as well. Further, the method may include recovery of the catalyst after filtration of the hydrogenated alpha dimethyl styrene dimer. The recovered catalyst may then be combined with fresh catalyst and used in another reaction. The amount of recovered catalyst, the amount of fresh catalyst needed and the number of times the catalyst can be reused can all be varied by user for optimal performance. Concentrations of catalyst may be between about 0.001 wt % to about 10 wt % or about 0.25 wt % to about 10 wt % of input on dry basis. In some cases 5% Ru/C or Rh/C catalyst is preferred. The Ru/C or Rh/C catalyst may be supplemented by other catalysts and be present in the reaction in any form. In some cases, Ru/C is more cost effective, though the amount of catalyst used and the recoverability of the catalyst may lead the user to select a different catalyst or combination of catalysts.

The alpha dimethyl styrene dimer added to the reactor to form a reaction mixture can be in an amount between about 50 grams and about 1000 grams, and more preferably about 50 grams to about 300 grams.

The heating of the reaction mixture can include: beginning with the formation of the reaction mixture in the reactor at ambient temperature and raising the temperature of the reaction mixture to about 60° C., or to about 100° C., or both in a stepwise fashion. The hydrogenation reaction of alpha dimethyl styrene dimer may occur at any temperature, preferably between about 47° C. and about 100° C. The rate of heating of the reaction mixture may be varied. The rate of heating may be defined as slowly, that is a gradual increase in temperature. The rate of heating may be between about 1 degree per hour and about 10 degrees per hour. In general, hydrogenation of double bonds may occur at about 60° C. and hydrogenation of aromatic rings occurs at about 100° C. Therefore the user may choose to raise the temperature from ambient room temperature to about 60° C. for a period of time followed by a gradual increase in temperature to about 100° C. for another period of time.

The hydrogenation reaction may proceed for about 2 to about 14 hours or until completion. Completion of a hydrogenation reaction is determined by measurement of hydrogen consumption. The lack of hydrogen consumption indicating the reaction is completed. The methods describe a Haste alloy reactor, but it is understood any appropriate vessel of any appropriate size may be used for the methods of the invention. Further, while the hydrogenation of HAD is specifically described, it will be appreciated that the methods may be used for hydrogenation of any unsaturated dimer.

The reaction time is dependent on, among other things, the amount of catalyst loading. The greater the catalyst load, the shorter the reaction time. For example, in Example 1, a 2 wt % loading of the input for 300 g of alpha dimethyl styrene dimer took 5 hours for completion. A 1 wt % loading for the same input amount of starting material took 7 hours, and 0.5 wt % loading took 7 hours. Thus, the amount of catalyst, time, temperature and pressure may be varied depending upon the time and cost constraints of the user.

The reaction mixture in the reactor is stirred or constantly stirred during the hydrogenation reaction using a turbine impeller operated at about 1,000 rpm. The hydrogenation reaction may proceed under a pressure of between about 10 and about 12 kg/cm$^2$.

The filtered hydrogenated alpha dimethyl styrene dimer product represents a yield from the starting alpha dimethyl styrene dimer of at least about 90% or greater, more preferably greater than 98%. The yield is also represented by any % greater than 90%, including 91%, 92%, 93%, 94%, 95%, 96%, 97%, 98%, 99%, 99.2%, 99.5%, 99.8% and 99.9%.

An alternative method of hydrogenated alpha dimethyl styrene dimer production includes adding to a reactor, under nitrogen, a catalyst comprising Ru/C or Rh/C, followed by addition under nitrogen of a solvent, and lastly addition of an alpha dimethyl styrene dimer to form a catalyst, solvent, and alpha dimethyl styrene dimer reaction mixture. The reaction mixture is heated under pressure until hydrogenation of the alpha dimethyl styrene dimer is complete. To recover the hydrogenated alpha dimethyl styrene dimer, the reaction mixture is filtered to remove catalyst through a celite bed under nitrogen. The solvent used may be iso propyl alcohol (IPA) or any other protic solvent. The ratio of starting material to solvent is preferably about 1:4.2 and more preferably 1:4.2.

was added. The reaction mixture was stirred with a stirrer at a constant rate of 1,000 RPM. The reaction mixture was heated to the temperature and pressure indicated in Table 1. Completion of the reaction was monitored by thin layer chromatography or NMR and when no more hydrogen consumption was indicated, the reaction mixture was filtered through a celite bed under nitrogen. The product was also analyzed by nuclear magnetic resonance (NMR) or gas chromatograph mass spectrometry (GCMS).

Figure 2B:
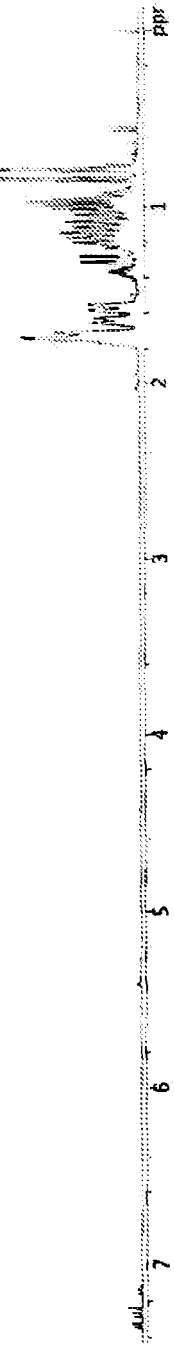
Figure 3A:
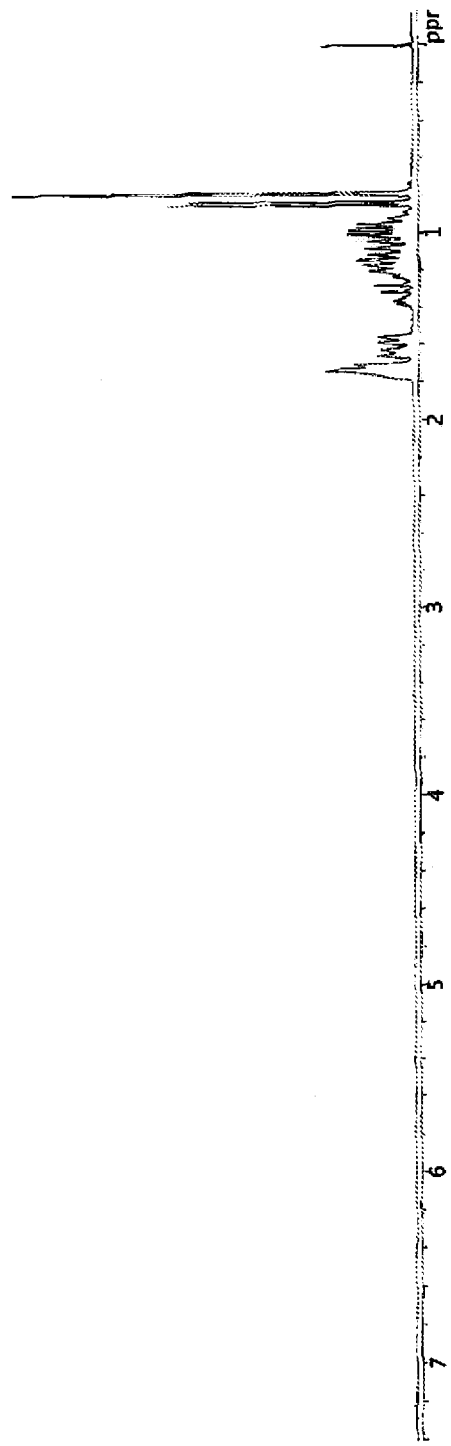
FIG. 3(A)-(B) shows the NMR spectra for (A) commercially available standard hydrogenated alpha dimethyl styrene dimer and (B) a hydrogenated alpha dimethyl styrene dimer prepared according to the methods of the present disclosure, Example 1, sample number 7.
Figure 3B:
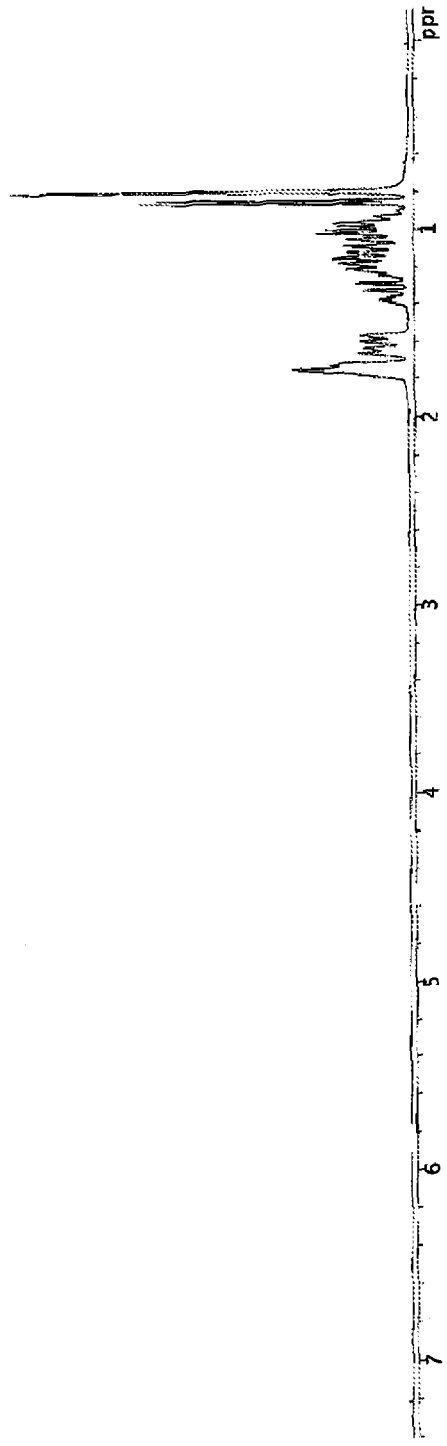

The results are shown in Table 1:

| No | Input AMS dimer (g) | Catalyst Loading | Solvent (ml) | Temp (° C.) | Pressure Kg/cm2 | RPM | Time (hr) | Yield gm (%) | Analytical data |
|---|---|---|---|---|---|---|---|---|---|
| 1 | 65.0 | 10% Ru/C (50% wt $H_2O$), (8 wt. % of Input on dry basis) | IPA (273 ml) | 60 | 10-11 | 1000 | 2 | 64.0 (93%) | NMR match standard |
| 2 | 65.0 | 10% Ru/C (50% wt $H_2O$) (4 wt. % of Input on dry basis) | IPA (273 ml) | 60 | 10-11 | 1000 | 4 | 62.0 (90%) | NMR FIG. 1 |
| 3 | 65.0 | 10% Ru/C (50 wt % $H_2O$) (2 wt. % of Input on dry basis) | IPA (273 ml) | 60 | 10-11 | 1000 | 12 | 57.4 (83%) Incomplete Rx. | NMR FIG. 2 Incomplete Reaction in 12 h |
| 4 | 65.0 | 10% Ru/C (50 wt % $H_2O$) (2 wt. % of Input on dry basis) | IPA (273 ml) | 100 | 10-11 | 1000 | 5 | 62.3 (90%) | NMR match standard |
| 5 | 300.0 | 10% Ru/C (50 wt % $H_2O$) (2 wt. % of Input on dry basis) | NA | 100 | 10-11 | 1000 | 5 | 313 | NMR match standard |
| 6 | 300.0 | 10% Ru/C (50 wt % $H_2O$) (1 wt. % of Input dry basis) | NA | 100 | 12 | 1000 | 6 | 315.6 (99%) | NMR match standard |
| 7 | 300.0 | 5% Ru/C (50 wt % $H_2O$), (1 wt % of Input on dry basis) | NA | 100 | 12 | 1000 | 7 | 314 (98.7%) | NMR FIG. 3 |
| 8 | 300.0 | 5% Ru/C (50 wt % $H_2O$) (0.5 wt % of the input on dry basis) | NA | 100 | 12 | 1000 | 12 | 312 (98.1%) | NMR match standard |
| 9 | 300.0 | 5% Ru/C (50 wt % $H_2O$) (0.25 wt % of the input) | NA | 100 | 12 | 1000 | 14 | — | Incomplete Reaction after 14 h |

In yet another method, hydrogenation of alpha dimethyl styrene dimer occurs by adding to a reactor, under nitrogen, a catalyst; the second step includes adding alpha dimethyl styrene dimer to the reactor, thereby forming a catalyst and alpha dimethyl styrene dimer reaction mixture; the third step includes heating the reaction mixture under pressure until hydrogenation of the alpha dimethyl styrene dimer is complete; and the fourth step includes filtering the reaction mixture through a celite bed under nitrogen thereby obtaining a hydrogenated alpha dimethyl styrene dimer product.

EXAMPLES

Example 1

Experimental Procedure
In a one-liter Haste alloy reactor, with turbine impeller, a catalyst was added. To the catalyst, isopropyl alcohol was added under nitrogen, in some of the examples. To the resultant catalytic solution, an alpha dimethyl styrene dimer In some cases the catalyst is supplied as 50% weight in water, the % dry basis may be calculated. According to Table 1, hydrogenation reactions carried out at both pressures of about 10 Kg/cm² to about 11 Kg/cm² and about 12 Kg/cm² produced complete reactions. Likewise, reactions carried out at both about 60° C., or about 100° C. or in the range between about 60° C. to about 100° C. produced complete reactions. A catalyst input of 0.25 wt % (sample 9) was insufficient to produce hydrogenated alpha dimethyl styrene dimer, while inputs between 0.5 wt % (sample 8) and 8 wt % (sample 1) did permit reaction completion. Table 1 demonstrates solvent to be an optional ingredient and not necessary for the hydrogenation of alpha dimethyl styrene dimers to occur. The hydrogenation reaction can be completed with different amounts of starting material and yields ranging from 90% to 99% of the starting material once reaction is complete. The time to reaction completion is variable.

The NMR of FIG. 2B shows an incomplete reaction of the sample number 3 because an aromatic peak is present. FIGS.

1B and 3B demonstrate that the hydrogenated end product of the process is indistinguishable from commercially available hydrogenation of alpha dimethyl styrene dimer for samples 2 and 7 of Table 1. FIGS. 1A, 2A, and 3A represent the commercially available HAD standard.

Certain embodiments have been described in the form of examples. It is impossible to depict every potential application. Thus, while the embodiments are described in considerable detail, it is not the intention to restrict or in any way limit the scope of the appended claims to such detail, or to any particular embodiment.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When "only A or B but not both" is intended, then the term "only A or B but not both" will be employed. Thus, use of the term "or" herein is the inclusive, and not the exclusive use. As used in the specification and the claims, the singular forms "a," "an," and "the" include the plural. Finally, where the term "about" is used in conjunction with a number, it is intended to include ±10% of the number. For example, "about 10" may mean from 9 to 11. The term HAD may be used to refer to a hydrogenated alpha dimethyl styrene dimer or hydrogenated dimers of alpha olefins, or any other term referring to the figure shown in Formula I or defined as HAD.

As stated above, while the present application has been illustrated by the description of embodiments, and while the embodiments have been described in considerable detail, it is not the intention to restrict or in any way limit the scope of the appended claims to such detail. Additional advantages and modifications will readily appear to those skilled in the art, having the benefit of this application. Therefore, the application, in its broader aspects, is not limited to the specific details and illustrative examples shown. Departures may be made from such details and examples without departing from the spirit or scope of the general inventive concept.

The invention claimed is:

1. A method for preparing hydrogenated alpha dimethyl styrene dimer comprising:
adding to a reactor under nitrogen a catalyst comprising Ru/C or Rh/C;
adding alpha dimethyl styrene dimer to the reactor thereby forming a catalyst and alpha dimethyl styrene dimer reaction mixture;
heating the reaction mixture under pressure until hydrogenation of the alpha dimethyl styrene dimer is complete; and
filtering the reaction mixture through a celite bed under nitrogen thereby obtaining a hydrogenated alpha dimethyl styrene dimer product.

2. The method of claim 1, further comprising concentrating under vacuum the filtered hydrogenated alpha dimethyl styrene dimer product.

3. The method of claim 1, further comprising recovery of the catalyst after the filtration of the reaction mixture and optionally using the recovered catalyst to form another reaction mixture.

4. The method of claim 1, the catalyst consisting of Ru/C or Rh/C.

5. The method of claim 1, the catalyst present in an amount between about 0.001 wt % to about 10 wt % of input.

6. The method of claim 1, the catalyst present in an amount about 5 wt %.

7. The method of claim 1, further comprising the step of:
adding solvent under nitrogen to the reactor,
wherein the solvent is added after addition of the catalyst to the reactor and before the addition of the alpha dimethyl styrene dimer to the reactor.

8. The method of claim 7, wherein the solvent is selected from the group consisting of:
isopropyl alcohol and protic solvents.

9. The method of claim 7, wherein the solvent present in an amount between about 1 mL and about 300 mL.

10. The method of claim 1, the alpha dimethyl styrene dimer added to the reactor in an amount between about 50 grams and about 1000 grams.

11. The method of claim 1, the alpha dimethyl styrene dimer added to the reactor in an amount between about 65 grams and about 1000 grams.

12. The method of claim 1, the heating processing including: beginning with the formation of the reaction mixture in the reactor at ambient temperature and raising the temperature of the reaction mixture to about 100° C.

13. The method of claim 1, the heating processing including: beginning with the formation of the reaction mixture in the reactor at ambient temperature and raising the temperature of the reaction mixture to about 60° C.

14. The method of claim 1, wherein the reaction proceeds for about 2 to about 14 hours until completion.

15. The method of claim 1, further comprising the step of:
monitoring reaction completeness by thin layer chromatography of a sample of the reaction mixture, wherein the reaction is complete when hydrogen consumption ceases.

16. The method of claim 1, further comprising the step of monitoring reaction completeness by testing the filtered hydrogenated alpha dimethyl styrene dimer product by nuclear magnetic resonance or gas chromatograph mass spectrometry.

17. The method of claim 1, wherein the reaction mixture in the reactor is under a pressure of between about 10 and about 12 Kg/cm$^2$.

18. The method of claim 1, wherein the reaction mixture in the reactor is constantly stirred.

19. The method of claim 1, wherein the filtered hydrogenated alpha dimethyl styrene dimer product represents a yield from the starting alpha dimethyl styrene dimer of about 90% or greater.

20. The method of claim 1, wherein
the first step is adding to a reactor under nitrogen a catalyst;
the second step is of adding alpha dimethyl styrene dimer to the reactor thereby forming a catalyst and alpha dimethyl styrene dimer reaction mixture;
the third step is heating the reaction mixture under pressure until hydrogenation of the alpha dimethyl styrene dimer is complete; and
the fourth step is of filtering the reaction mixture through a celite bed under nitrogen thereby obtaining a hydrogenated alpha dimethyl styrene dimer product.

* * * * *